US005411036A

United States Patent [19]

Wilkes

[11] Patent Number: 5,411,036

[45] Date of Patent: May 2, 1995

[54] MAYO STAND COVER

[76] Inventor: Kenneth R. Wilkes, 5416 Union Pacific Ave., Commerce, Calif. 90022

[21] Appl. No.: 297,328

[22] Filed: Aug. 29, 1994

Related U.S. Application Data

[63] Continuation of Ser. No. 977,924, Nov. 18, 1992, abandoned.

[51] Int. Cl.$^{6}$ ........................ A61B 19/00; A61B 19/08

[52] U.S. Cl. ........................................ 128/849; 128/856

[58] Field of Search ................................ 128/849–856; 383/116, 121; 206/439, 440

[56] References Cited

U.S. PATENT DOCUMENTS 3,003,681 10/1961 Orsini .................................. 383/121
3,189,252 6/1965 Miller ......................... 128/DIG. 24
3,244,169 4/1966 Baxter ................................ 128/850
3,357,152 12/1967 Geigel ................................ 383/121
3,375,969 4/1968 Davis ................................. 383/121
3,381,886 5/1968 Goglio ................................ 383/121
3,538,912 11/1970 Becker ............................... 128/853
3,540,441 11/1970 Collins ............................... 128/855
3,738,405 6/1973 Ericson .............................. 128/852
3,747,655 7/1973 Hadtke ............................... 128/855
4,489,720 12/1984 Morris ............................... 128/855
4,657,003 4/1987 Wirtz ................................. 128/869
4,926,882 5/1990 Lawrence ........................... 128/850
5,170,804 12/1992 Glassman ........................... 128/849

*Primary Examiner*—Michael A. Brown
*Attorney, Agent, or Firm*—Saul Epstein

[57] ABSTRACT

A Mayo Stand cover in the form of a bag made of plastic tubing wherein a portion of the area of the bag which covers the tray is necked down to provide a closer fit to the tray than does the remainder of the bag whereby the bag will fit smoothly on the tray and not be prone to shift.

14 Claims, 1 Drawing Sheet

13 14 10 17 18 19 15 16 19 19 19 20 12 20

MAYO STAND COVER

This is a continuation of application Ser. No. 07/977,924, filed on Nov. 18, 1992, now abandoned.

BACKGROUND OF THE INVENTION

Instruments used by surgeons during surgical procedures are commonly laid out on a moveable tray table called a "Mayo stand". A Mayo Stand includes a tray on which instruments to be used during surgery are placed, a vertical leg from which the tray is cantilevered, and a base, usually including casters, which supports the vertical leg. In order to insure sterility, just prior to surgery, the tray and the vertical leg of the stand are ordinarily covered with a disposable sterile bag made of plastic tubing. Since the tray is horizontal and the leg is vertical, the plastic tubing must be made relatively large so that it can easily be slipped around the corner where the tray and the leg join.

A typical Mayo Stand tray may be 13 inches wide by 19 inches long and supported at one end (at table height) by one or two vertical members. The plastic tubing commonly used to make a cover for such a stand has a circumference of about 46 to 48 inches. That is, when flattened and made into a bag, the tubing is 23 to 24 inches wide. The extra 10 or so inches in width are required to assure that there will be no binding as the cover is installed.

The extra material, while needed for ease in installation, also creates a problem. The problem is that the portion of the cover which covers the tray tends to not center on the tray; it rather tends to twist and create folds in the area of the tray where the instruments are to be placed. There is also the risk that the cover might shift during surgery if it is brushed against, with disastrous results.

It is therefore an object of this invention to provide a Mayo Stand cover which is self centering on the tray, and which provides a flat smooth, positionally stable, surface on which to place surgical instruments.

SUMMARY OF THE INVENTION

Automatic centering of the Mayo Stand cover on the tray is accomplished in the present invention by reducing the inside diameter of the tubing in the region near the closed end of the bag. The preferred means for reducing the tubing diameter is to make a pair of lengthwise parallel seams along the bag which extend from the closed end a short distance toward the open end of the bag. The "necked down" section of the tubing formed by the lengthwise seams is somewhat shorter than the length of the tray so that in the region of the bag that must make the horizontal/vertical transition, there is enough material to ease the turn. Hence, the cover is large enough to install easily, but still does not have extra material around the tray which can form unwanted folds, and allow unwanted movement.

An additional feature of the present invention is the inclusion of some weight at the edges of the cover in the necked down area, which tends to make the end corners of the bag to fold down out of the way.

DETAILED DESCRIPTION OF THE INVENTION

Figure 2:
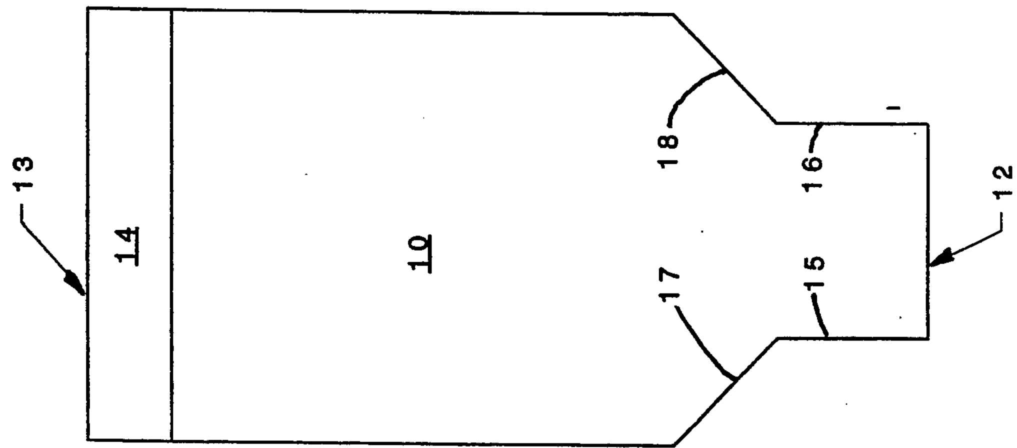
FIG. 2 shows a top plan view of a second embodiment of the invented Mayo Stand cover

The figures show top plan views of the presently preferred embodiments of the invented Mayo Stand cover. The embodiments are identical in many ways, and like numbers in each figure denote like features. For conceptual purposes, illustrative dimensions are recited in this application, but it should be understood that in a particular exemplar of the invention, the dimensions given may or may not be appropriate.

The invented Mayo Stand cover is similar in many ways to prior art Mayo Stand covers in that it basically has the form of a large elongated plastic bag. The bag is preferably fabricated from a flattened plastic tube of suitable length, e.g., 4 feet. It is, of course, possible to fabricate the bag from two flat sheets placed face to face and seamed, but properly sized tubing is easily available, and is a convenient starting material. The invention will be described, therefore, as if fabricated from a tube.

As seen in the plan views shown in the figures, the flattened tube has a top panel 10 and a corresponding bottom panel 11 (which cannot be seen in the figures since it lies under the top panel). One end of the tube (12) is sealed transversely so as to form an elongated open mouthed bag. A suitable width of the flattened tube may, for example, be 23 inches (i.e., a 46 inch circumference tube). The open end of the bag 13 is folded over outwardly, forming a cuff 14 about 4 inches deep. The cuff is used as a convenient means to hold the bag when installing it onto a Mayo Stand. When in place on a Mayo Stand, the bag encloses not only the tray area, but the leg which supports the tray. This construction is used to assure that contamination on the Mayo Stand leg does not somehow find its way onto the tray top sterile area.

As so far described, the Mayo Stand cover is in accordance with prior art Mayo Stand covers. The dimensions mentioned are dimensions which are suitable for use in covering a Mayo Stand wherein the instrument holding tray is about 13 inches wide by 19 inches long. As will no doubt be appreciated, the extra 10 inches in width (23 inches minus 13 inches) allows the cover to assume undesired orientations with respect to the tray. Despite this disadvantage, the extra width is provided so that there will be no binding when, during installation, it is necessary to slip the cover over the corner joining the tray and the stand legs. It is necessary that the bag have a relatively large diameter in order to make this right angle turn easily. The means used in the invented cover for causing it to assume the desired orientation with respect to the instrument tray in the installed position is described in the next paragraph.

A pair of spaced parallel seams 15 and 16, which attach panels 10 and 11, are provided near the closed end of the bag. The parallel seams 15 and 16 are the preferred means for laterally reducing the internal size of the bag. These seams, which are preferably substantially symmetrical with respect to the long axis of the bag, have a length somewhat less than the length of the tray onto which the cover is to be placed, and are spaced apart 2 to 3 inches more than the tray is wide. That is, if the tray is 13 inches wide by 19 inches long, the seams would conveniently be about 6 to 8 inches long, and spaced about 10 to 11 inches apart. A pair of "lead in" seams 17 and 18 guide the tray into the space between the seams 15 and 16. The angle between the lead in seams is not critical, an included angle of about 60 degrees having been found satisfactory. Restricting the space for the tray at the end of the bag insures that the bag will fit over the tray in a symmetrical manner and that it will lie smoothly on the tray and resist unwanted movement.

As an additional element to aid in causing the cover to lie smoothly on the tray surface, and to assure that the extra material outboard of the seams 15 and 16 do not get in the way during surgery, one or more weights 19 (shown dotted) are sealed inside the bag at the each of the bottom corners of the bag, and, if desired, additionally along the bag edges, as illustrated. These weights may be made of metal, plastic, or any other available relatively dense material. The weights could even be granular or liquid if desired. When the cover is in place on a Mayo Stand, the weights 19 will cause the corners of the bag to turn downward out of the way. Seams 20 may be used to keep the weights from moving with respect to the bag.

Figure 1:
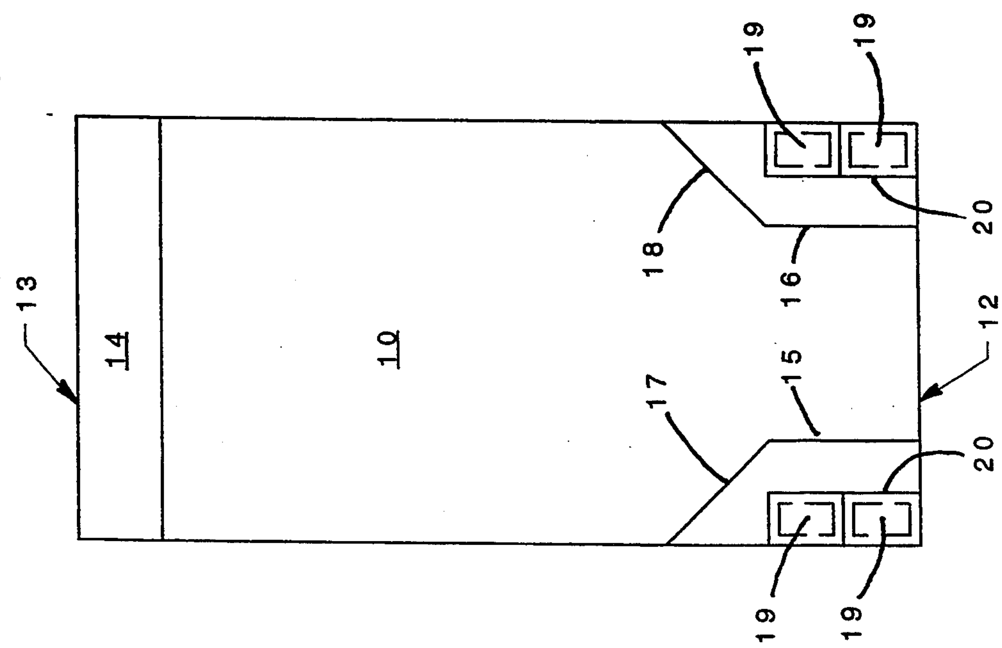
FIG. 1 shows a top plan view of a first embodiment of the invented Mayo Stand cover.

Another way of keeping the material outboard of seams 15 and 16 out of the way, is to remove it as indicated in the embodiment of FIG. 2. This second embodiment is identical to the embodiment of FIG. 1 except that the material outside of the seams 15 and 16 has been cut away. This construction is advantageous because Mayo Stand covers must be disposed of after surgery, and the cost to hospitals for disposal is based on the weight of the disposed of material. The price per pound is relatively large, and therefore even small weight savings are important.

Mayo Stand covers are normally folded and stored in a sterilized condition pending use. Prior art folding schemes, such as described in U.S. Pat. Nos. 3,742,944 or 3,747,655 (and others) can be used in connection with the present invention, the Mayo Stand cover of this invention not being restricted to any particular method of folding and/or storage. The present invention is directed to means for assuring that the cover, after installation, provides a satisfactory instrument placement area, rather than being directed to a method for conveniently installing it.

I claim:

1. A cover for a surgical instrument Mayo Stand of the type which includes a horizontally disposed tray cantilevered off a vertical support which comprises:

an elongated flexible flattened plastic bag comprised of a front panel and a back panel, and having an open end and a closed end, the internal size of said bag being large enough to allow said bag to be slipped over said instrument tray and said vertical support without binding; and means adjacent the closed end of said bag for laterally reducing the internal size of said bag for a distance from the closed end of said bag whereby said bag will be automatically centered with respect to the width of said bag, said distance being less than the length of said tray, said means including means for holding said front panel to said back panel at one or more points inboard of the edges of said panels.

2. A cover for a surgical instrument stand as recited in claim 1 where said means for reducing the internal size of said bag comprises a pair of spaced seams which attach said front panel to said back panel and which extend generally parallel to the long axis of said plastic bag,

3. A cover for a surgical instrument stand as recited in claim 2 and further including weighting means attached to said bag outboard of said spaced seams adjacent to the closed end of said bag.

4. A cover for a surgical instrument stand as recited in claim 2 wherein the panel material outboard of said spaced seams has been removed.

5. A cover for a surgical instrument stand as recited in claim 2 and further including a pair of seams extending at an angle to the long axis of said bag from the end of each of said spaced seams to provide a transition between the unreduced internal size of said bag and the size of said bag between said spaced seams.

6. A cover for a surgical instrument stand as recited in claim 5 and further including weighting means attached to said bag outboard of said spaced seams adjacent to the closed end of said bag.

7. A cover for a surgical instrument stand as recited in claim 5 wherein the panel material outboard of said spaced seams has been removed.

8. A cover for a surgical instrument Mayo Stand of the type which includes a horizontally disposed tray cantilevered off a vertical support which comprises:

a flexible plastic bag having a length greater than its width in its flattened state, and being comprised of a front panel and a back panel, said bag having an open end extending across its width and a closed end extending across its width, the width of said bag at its open end and for a predetermined distance from said open end being large enough to allow said bag to be slipped over said tray and said vertical support without binding, and long enough to cover said tray and at least a portion of said vertical support; and means adjacent the closed end of said bag for automatically centering the long axis of said bag on said tray of said Mayo Stand when said bag is slipped over said tray and vertical support.

9. A cover for a surgical instrument Mayo Stand as recited in claim 8 wherein said means for automatically centering the long axis of said bag on said tray of said Mayo Stand is comprised of means for attaching said front panel to said back panel at at least two points spaced laterally with respect to the long axis of said bag in its flattened state, said two points being spaced less than the width of said bag.

10. A cover for a surgical instrument Mayo Stand as recited in claim 9 wherein each of said at least two points is comprised of an elongated seam which extends generally parallel to the long axis of said plastic bag, the spacing of said seams being less than the width of said bag.

11. A cover for a surgical instrument Mayo Stand as recited in claim 10 and further including weighting means attached to said bag outboard of said spaced seams adjacent to the closed end of said bag.

12. A cover for a surgical instrument Mayo Stand of the type which includes a horizontally disposed tray cantilevered off a vertical support which comprises:

a flexible plastic bag having a length greater than its width in its flattened state, and being comprised of a front panel and a back panel, said bag having an open end extending across its width and a closed end extending across its width, the width of said bag being large enough to allow said bag to be slipped over said tray and said vertical support without binding; and means adjacent the closed end of said bag for reducing the width of said bag for a predetermined distance from the closed end of said bag, said means for reducing the width of said bag comprising means for attaching said front panel to said back panel at at least two points spaced laterally with respect to the long axis of said bag less than the width of said bag in its flattened state, and spaced from said closed end of said bag.

13. A cover for a surgical instrument Mayo Stand as recited in claim 12 wherein said means for attaching said front panel to said back panel comprises a pair of spaced seams which attach said front panel to said back panel and which extend generally parallel to the long axis of said plastic bag.

14. A cover for a surgical instrument Mayo Stand as recited in claim 13 and further including weighting means attached to said bag outboard of said spaced seams adjacent to the closed end of said bag.

* * * * *